(12) United States Patent
Vogler et al.

(10) Patent No.: US 9,188,776 B2
(45) Date of Patent: Nov. 17, 2015

(54) SYSTEM AND METHOD FOR SCANNING A BEAM OF ULTRA-SHORT PULSE LIGHT

(71) Applicant: Novartis AG, Basel (CH)

(72) Inventors: Klaus Vogler, Eckental/Eschenau (DE);
Claudia Gorschboth, Nuremberg (DE);
Christof Donitzky, Eckental/Eschenau (DE)

(73) Assignee: Novartis AG (CH)

( * ) Notice: Subject to any disclaimer, the term of this patent is extended or adjusted under 35 U.S.C. 154(b) by 0 days.

(21) Appl. No.: 14/389,730

(22) PCT Filed: Mar. 15, 2013

(86) PCT No.: PCT/EP2013/055379
§ 371 (c)(1),
(2) Date: Sep. 30, 2014

(87) PCT Pub. No.: WO2014/139582
PCT Pub. Date: Sep. 18, 2014

(65) Prior Publication Data
US 2015/0062680 A1    Mar. 5, 2015

(51) Int. Cl.
*G02B 26/08* (2006.01)
*G02B 26/10* (2006.01)
*A61F 9/008* (2006.01)
*G02B 27/00* (2006.01)

(52) U.S. Cl.
CPC .......... *G02B 26/101* (2013.01); *A61F 9/00825* (2013.01); *G02B 26/0833* (2013.01); *G02B 27/0031* (2013.01); *A61F 2009/0087* (2013.01); *A61F 2009/00872* (2013.01)

(58) Field of Classification Search
CPC .......... G02B 26/0833; G02B 27/0031; G02B 26/101; A61F 9/008
USPC ................... 359/202.1, 206, 1; 606/4
See application file for complete search history.

(56) References Cited

U.S. PATENT DOCUMENTS

| 4,834,474 A | 5/1989 | George et al. |
| 5,734,503 A | 3/1998 | Szipöcs |
| 2012/0212791 A1* | 8/2012 | Okada ........................ 359/202.1 |

FOREIGN PATENT DOCUMENTS

WO    2011069516 A1    6/2011

OTHER PUBLICATIONS

Hermann, et al.; "Adaptive-Optics Ultrahigh-Resolution Optical Coherence Tomography"; Optics Letters; The Optical Society; vol. 29; No. 18; Sep. 15, 2004; pp. 2142-2144.
Yasuyuki Ozeki, et al.; Broadband Spectral Phase Control with a Tapered Deformable Mirror in a 4-f Pulse Shaper; Lasers and Electro-Optics—Pacific Rim; Cleo/Pacific Rim 2007 Conference; Aug. 1, 2007; pp. 1-2.

(Continued)

*Primary Examiner* — Euncha Cherry

(57) ABSTRACT

An embodiment of a scanning optical system comprises: an optical source providing a beam of pulsed light of ultra-short pulse duration; a deflector for deflecting the beam through a scan angle; a lens system including a focusing objective for focusing the deflected beam; a dispersion compensating device for reducing dispersion-related distortion of a pulse of the beam by the lens system, the dispersion compensating device including a deformable, dispersive mirror and an actuator device for the mirror; and a controller for controlling the actuator device to change a shape of the mirror in accordance with the scan angle.

10 Claims, 3 Drawing Sheets

(56) References Cited

OTHER PUBLICATIONS

Zeek, et al.; Pulse Compression by Use of Deformable Mirrors; Optics Letters; The Optical Society; vol. 24; No. 7; Apr. 1, 1999; pp. 493-495.
Stefano Bonora, et al.; Ultrabroadband Pulse Shaping with a Push-Pull Deformable Mirror; Optics Express; vol. 18; No. 22; Oct. 25, 2010; pp. 23147-23152.
Gabriel Tempea; "State-of-the-art dispersion management with Broadband Multilayer Reflectors"; Bios 2012; Jan. 21-22, 2012; pp. 1-27; Femtolasers (www.femtolasers.com); ISSN 0036-1860.
Wolleschensky et al.; "Characterization and optimization of a laser-scanning microscope in the femtosecond regime"; Applied Physics B Lasers and Optics; Feb. 2, 1998; pp. 87-94.
Müller et al.; "Dispersion pre-compensation of 15 femtosecond optical pulses for high-numerical-aperture objectives"; Journal of Microscopy; Aug. 1998; pp. 141-150; vol. 191; Pt 2.
Fuchs; ''Combined software tools model effects of optics on ultrashort pulses; Photonics Spectra; (2005); pp. 31-32; http://www.photonics.com/Article.aspx?AID=22467 [online].
Netz et al; Diffraction of ultrashort laser pulses and applications for measuring pulse front distortion and pulse width; Applied Physics B Lasers and Optics; Jan. 6, 2000.
Netz et al; "Measurement of the pulse-front distortion in high-numerical-aperture optics"; Applied Physics B Lasers and Optics; Feb. 23, 2000.
Tempea; "State-of-the-art dispersion management with Broadband Multilayer Reflectors"; Spie Bios; Jan. 21-22, 2012; (Product demonstration).
Trebino; Frequency Resolved Optical Grating; Newport Experience Solutions; pp. 1-4; Online: http://search.newport.com/?q=opticar/%20gating.
Walter; Fundamentals of Optical Transmission Systems; Digital GmbH & CoKG; Mar. 1, 2005; pp. 1-13.
Wolleschensky et al.; Group-Velocity Dispersion and Fiber Delivery in Multiphoton Laser Scanning Microscopy; Confocal and Two-Photon Microscopy; (2002); ISBN 0-471-40920; Chapter 8; pp. 171-190.

* cited by examiner

SYSTEM AND METHOD FOR SCANNING A BEAM OF ULTRA-SHORT PULSE LIGHT

CROSS REFERENCE TO RELATED APPLICATIONS

This application is a section 371 national stage phase of International Application No. PCT/EP2013/055379, filed 15 Mar. 2013, titled "SYSTEM AND METHOD FOR SCANNING A BEAM OF ULTRA-SHORT PULSE LIGHT", which is hereby incorporated by reference in its entirety.

The present disclosure pertains to systems and methods for scanning a beam of ultra-short pulse light.

For ultra-short pulses of electromagnetic radiation, material dispersion may cause unwanted distortion of the pulses when they propagate through glass or other optical materials in an optical system. The amount of distortion depends on the spectral bandwidth of the pulse and becomes particularly significant as the pulse duration is reduced to values in the two-digit femtosecond range or shorter. The adverse effects of material dispersion include propagation time difference (PTD), or group delay (GD), and group velocity dispersion (GVD). The GVD is comprised of different orders of dispersion through the optical material. Group delay dispersion (GDD) is the second order of dispersion and causes a temporal broadening of a pulse propagating through an optical material. Higher orders include third-order dispersion (TOD) and fourth-order dispersion (FOD). A more detailed discussion of the effects of the PTD and GVD can be found in US 2011/0058241, the content of which is hereby incorporated by reference.

The path length traversed in a lens by a ray may depend on the radial distance from an optical axis of the lens. For example, a converging lens has greater thickness in a center portion and smaller thickness in a peripheral portion of the lens. In a diverging lens, the path length is greater at a peripheral portion of the lens and becomes smaller towards the center of the lens. Depending on the radial position relative to the optical axis of the lens, a ray propagating through the lens may thus experience a different amount of dispersion.

The path length traversed by a ray in a lens may also depend on the angle of propagation of the ray in the lens material with respect to the optical axis of the lens. The angle at which a ray traverses the lens depends on the angle of incidence of the ray on the lens. Rays that are incident on the lens at the same position, but at different angles of incidence, thus experience different path lengths in the lens. The angle of incidence may vary as a beam propagating pulses of the light is scanned across a plane that is orthogonal to the direction of propagation of the beam. Different angles of incidence thus may represent different scan angles. Hence, depending on the scan angle, a ray propagating through the lens may experience a different amount of dispersion. In particular, the ray may experience different amounts of GD for different values of the scan angle.

Dispersive mirrors are useful for reducing the GDD introduced by an optical system. To this end, the dispersive mirror may be designed to introduce a negative chirp, which compensates at least partially a positive chirp (temporal broadening) introduced by the optical system for a pulse travelling through the optical system. US 2011/0058241 A1 describes chirped multilayer mirrors with GDD values that vary with incident angle.

The present disclosure provides a scanning optical system comprising: an optical source providing a beam of pulsed light of ultra-short pulse duration; a deflector for deflecting the beam through a scan angle; a lens system including a focusing objective for focusing the deflected beam; a dispersion compensating device for reducing dispersion-related distortion of a pulse of the beam by the lens system, the dispersion compensating device including a deformable, dispersive mirror and an actuator device for the mirror; and a controller for controlling the actuator device to change a shape of the mirror in accordance with the scan angle.

Changing the shape of the deformable, dispersive mirror can be effective to introduce, or alter, a relative delay between wave packets incident at different positions of the mirror. In this way, the relative temporal displacement between wave packets incident at different positions of the mirror can be adjusted and variations of the spatial distribution of the group delay (GD) versus scan angle of the lens system can be compensated at least partially. Changing the shape of the deformable, dispersive mirror may include moving back or forth one or more reflecting surface portions of the mirror relative to one or more other reflecting surface portions of the mirror.

In certain embodiments, the deformable, dispersive mirror has a multilayer structure providing a dispersion characteristic that varies with position on a reflecting surface of the mirror. For example, the multilayer structure of the deformable, dispersive mirror may introduce at least one of a non-uniform GD, a non-uniform GDD, and a non-uniform TOD across the reflecting surface. A non-uniform GD of the mirror may be useful to compensate variations of GD versus different values of radial offset from an optical axis of the lens system. Similarly, a non-uniform GDD and TOD of the mirror may be useful to compensate variations of GDD and TOD, respectively, versus different values of radial offset from the optical axis of the lens system. Spatial variations of the GD, GDD or TOD may be particularly prominent in large-aperture optics as are used, e.g., in femtosecond laser systems designed for ophthalmic surgery.

In certain embodiments, the dispersion compensating device further includes a bulk compensator having a spatially uniform dispersion characteristic for compensating a bulk of at least one of a group delay and a group delay dispersion introduced by the lens system.

In certain embodiments, the optical source is a laser source and the light has a center wavelength suitable for creating incisions in human eye tissue.

The present disclosure provides also a scanning method comprising: providing a beam of pulsed light of ultra-short pulse duration; deflecting the beam through a scan angle; focusing the deflected beam with a focusing objective; providing a deformable mirror; and controlling a shape of the deformable mirror in accordance with the scan angle to compensate at least partially variations of the spatial distribution of a group delay of the focusing objective versus different scan angles.

It is to be noted that in certain embodiments of the present disclosure the deformable, dispersive mirror can be replaced with a deformable, non-dispersive mirror. In such embodiments, the deformable mirror can still be used to adjust the length of an air space between the mirror and a subsequent optical member (e.g. lens) locally, i.e. individually for different spatial positions, based on the scan angle of the light beam. In this way, variations of the spatial distribution of the group delay of the optical system can be accommodated, which variations may come with different scan angles. Yet the deformable mirror introduces no group velocity dispersion for pulses incident on the mirror in these embodiments.

Embodiments of the present disclosure will now be described by way of example in greater detail with reference to the attached drawings, in which.

Figure 1:
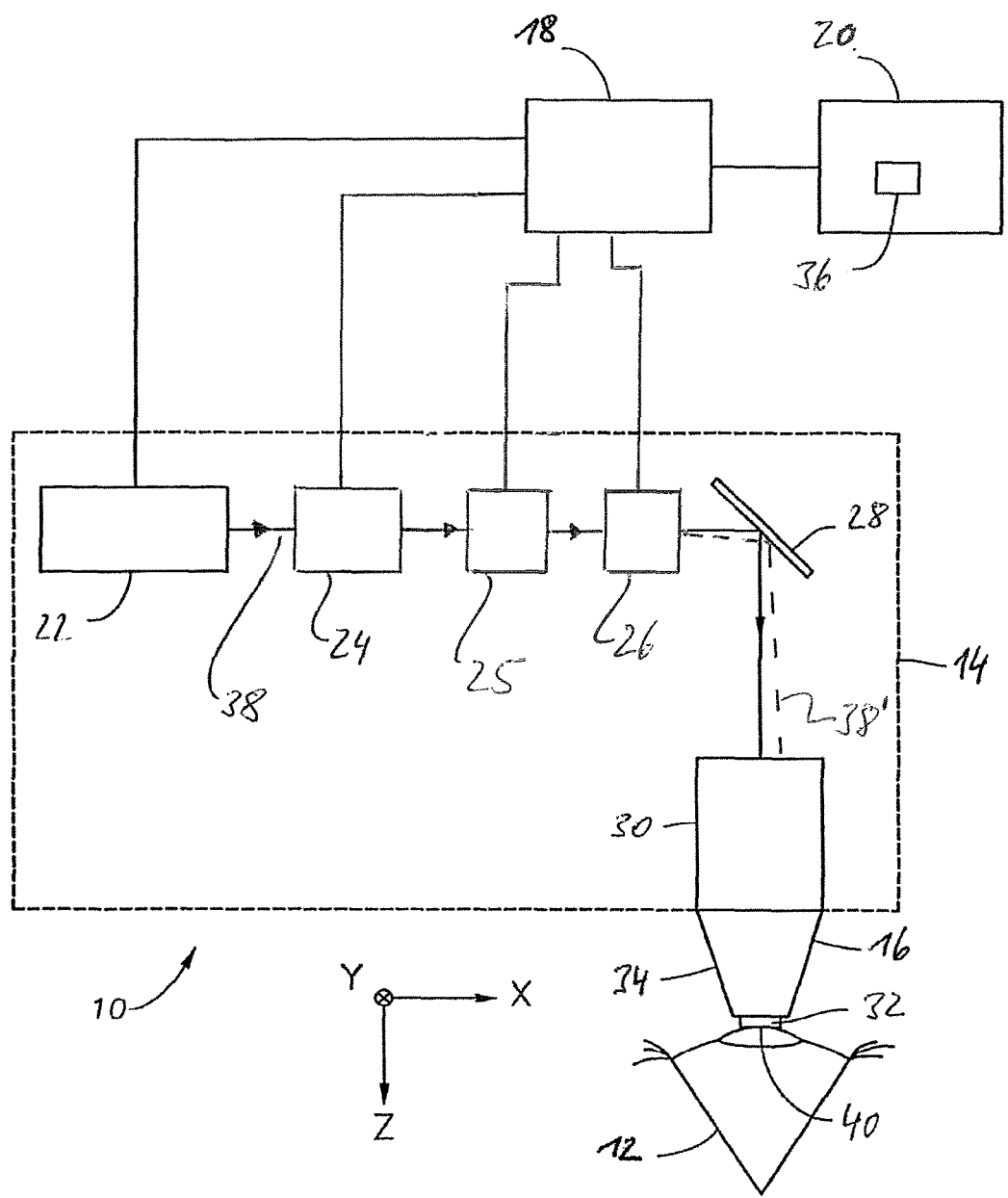
FIG. 1 illustrates an example of a scanning optical system that is useful for creating incisions in a human eye, according to an embodiment.

Referring now to the drawings, example embodiments of the disclosed system and method are shown in detail. The following description is in no way intended to be exhaustive or to otherwise limit or restrict the accompanying claims to the specific embodiments shown in the drawings and disclosed herein. Although the drawings represent possible embodiments, the drawings are not necessarily to scale and certain features may be simplified, exaggerated, removed, or partially sectioned to better illustrate the embodiments. In addition, certain drawings may be in schematic form.

FIG. 1 illustrates an example embodiment of a scanning optical system 10 that can scan and focus a beam of ultra-short pulses of laser light. In the illustrated embodiment, the scanning optical system 10 includes a laser device and a control computer. The laser device can create incisions in a cornea, a human lens, or other tissue structures of a human eye using the laser light. As used herein, ultra-short is intended to mean a pulse duration of less than 100, 80, 50, or 20 femtoseconds (fs). In certain embodiments, the pulse duration is in the single-digit femtosecond range (i.e. less than 10 fs) or in the attosecond (as) range.

In the illustrated example of FIG. 1, the scanning optical system 10 performs laser surgery on a human eye 12. The scanning optical system 10 includes a laser device 14, a patient adapter 16, a control computer 18, and a memory 20, which may be coupled as shown. The laser device 14 includes a laser source 22, a beam expander 24, a dispersion compensating device 25, a scanner 26, one or more optical mirrors 28, and a focusing objective 30 coupled as shown. The patient adapter 16 includes a contact element 32 and a support sleeve 34, which may be coupled as shown. The memory 20 stores a control program 36.

The laser source 22 generates a laser beam 38 with ultra-short pulses. The focal point of the laser beam 38 may create a laser-induced optical breakdown (LIOB) in tissues such as the cornea or other tissue structures of the eye 12. The laser beam 38 may have any suitable wavelength, such as a wavelength in the range of 300-1900 nanometers (nm), for example a wavelength in the range of 300-650, 650-1050, 1050-1250, 1100-1500 nm, or 1500-1900 nm. The laser beam 38 may also have a relatively small focus volume, e.g. 5 micrometers (μm) or less in diameter.

The beam expander 24, dispersion compensating device 25, transverse scanner 26, optical mirrors 28, and focusing objective 30 are in the beam path of the laser beam 38.

The beam expander 24 is configured to expand the width or diameter of the laser beam 38. An example of the beam expander 24 is an afocal telescope of the Galilean type.

The scanner 26 is configured to transversely control the focal point of the laser beam 38. "Transverse" refers to a direction at right angles to the direction of propagation of the laser beam 38, and "longitudinal" refers to the direction of beam propagation. The transverse plane may be designated as an x-y plane, and the longitudinal direction may be designated as the z-direction. The scanner 26 may transversely deflect the laser beam 38 in any suitable manner. For example, the scanner 26 may include a pair of galvanometrically actuated scanner mirrors that can be tilted about mutually perpendicular axes. As another example, the scanner 26 may include an electro-optical crystal that can electro-optically steer the laser beam 38.

The laser device 14 can also direct the laser beam 38 longitudinally to displace the focal point of the beam 38 in the z-direction. For longitudinal scanning, the laser device 14 may include a longitudinally adjustable lens, a lens of variable refractive power, or a deformable mirror that can control the z-position of the beam focus. In certain embodiments, the beam expander 24 includes a lens assembly comprised of two or more lenses, wherein one of the lenses of the beam expander 24 is disposed to be longitudinally adjustable or has variable refractive power. In other embodiments, the scanner 26 includes a longitudinal scanning member such as, e.g., a deformable mirror.

The one or more optical mirrors 28 direct the laser beam 38 towards the focusing objective 30. For example, an optical mirror 28 may be an immovable deviating mirror or a movable deviating mirror. As an alternative, an optical element that can refract and/or diffract the laser beam 38 may be provided in place of an optical mirror 28.

The focusing objective 30 focusses the laser beam 38 onto a target area of the eye 12. The focusing objective 30 may be separably coupled to the patient adapter 16. The focusing objective 30 may be any suitable optical device, such as an F-Theta objective. In certain embodiments, the focusing objective 30 is a multi-lens device composed of a plurality of refractive lenses.

The patient adapter 16 interfaces with the cornea of the eye 12. The sleeve 34 couples to the focusing objective 30 and retains the contact element 32. The contact element 32 is transparent or translucent to the laser light and has an abutment face 40 that interfaces with the cornea and may level a portion of the cornea. In certain embodiments, the abutment face 40 is planar and forms a planar area on the cornea. The abutment face 40 may be on an x-y plane, so that the planar area is also on an x-y plane. In other embodiments, the abutment face 40 need not be planar, e.g., may be convex or concave.

The control computer 18 controls controllable components of the laser device 14 such as, e.g., the laser source 22, beam expander 24, dispersion compensating device 25, scanner 26, and optionally at least one of optical mirror(s) 28, in accordance with the control program 36. The control program 36 contains computer code that instructs the controllable components to focus the pulsed laser radiation at a region of the eye 12 to photodisrupt at least a portion of the region.

The scanning components of the scanning optical system 10 may direct the laser beam 38 to form incisions of any suitable geometry. Any suitable portion of the tissue of the eye 12 may be photodisrupted. The optical system 10 may photodisrupt a tissue layer by moving the focus of the laser beam 38 along a given scan path. As the laser beam 38 travels along the scan path, the laser light pulses create photodisruptions in the tissue of the eye 12. Juxtaposition of a plurality of photodisruptions allows to create an incision of any desired geometry in the eye 12.

The dispersion compensating device 25 is disposed such that the pulses propagated by the laser beam 38 travel through the dispersion compensating device 25. The dispersion compensating device 25 adds amounts of group delay and group velocity dispersion to the pulses traversing the dispersion compensating device 25. More specifically, the dispersion compensating device 25 introduces appropriate amounts of GD and GDD that partially or completely compensate the amounts introduced in the rest of the laser device 14 for the pulses. The dispersion compensating device 25 may additionally add appropriate amounts of TOD. As output from the laser device 14, the laser pulses thus have a minimum amount of dispersion-related distortion.

In certain embodiments, the dispersion compensating device 25 may have a single compensator adding all the amount of dispersion provided by the dispersion compensating device 25. In other embodiments, the dispersion compensating device 25 may include two or more compensators which add separate amounts of dispersion. In one example, the dispersion compensating device 25 has a bulk compensator and a residual compensator. The bulk compensator introduces a bulk of the dispersion that is required to reduce the dispersion-related distortion of the pulses at the output of the laser device 14 to a minimum. The dispersion introduced by the bulk compensator is spatially uniform, i.e. is the same for all positions of incidence of a wave packet of the laser beam 38 on the bulk compensator. The residual compensator introduces residual amounts of dispersion. The dispersion added by the residual compensator is spatially non-uniform, i.e. is different for different positions of incidence of a wave packet of the laser beam 38 on the residual compensator. In certain embodiments, the dispersion added by the residual compensator has rotational symmetry and varies in a radial direction with respect to an axis of the symmetry.

Figure 2:
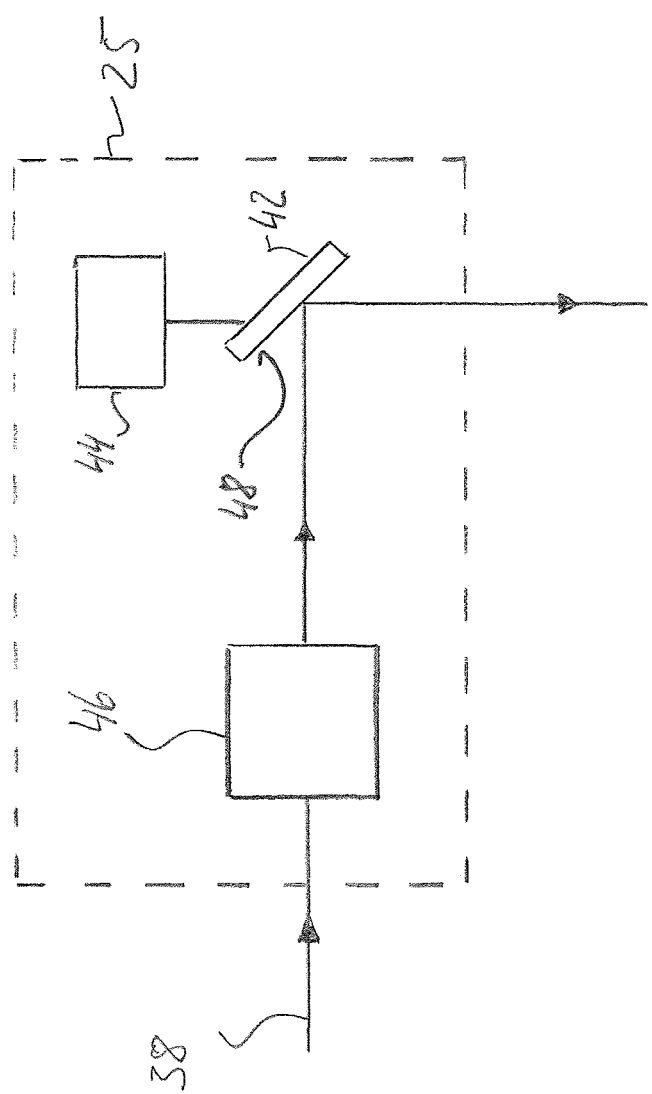
FIG. 2 illustrates details of a dispersion compensating device according to an embodiment.

Reference is now made additionally to FIG. 2 which illustrates an example embodiment of the dispersion compensating device 25. As shown in FIG. 2, the dispersion compensating device 25 comprises a deformable, dispersive (or "chirped") mirror 42, an actuator device 44, and a bulk compensator 46. The deformable, dispersive mirror 42 has a reflecting surface 48 formed by a multi-layer structure of a plurality of thin dielectric layers having refractive indices which are different from layer to layer. The actuator device 44 is connected with the control computer 18 and allows to move back and forth selected portions of the reflecting surface 48 relative to other surface portions, to thereby change the shape of the reflecting surface 48. In example embodiments, the actuator device 44 may include a plurality of individually controllable actuating members, wherein each actuating member acts on a different portion of the reflecting surface 48. The deformable, dispersive mirror 42 can be of any suitable type. In certain embodiments, the mirror 42 may include a segmented reflecting surface, wherein each segment can be moved back or forth independently of other segments. In other embodiments, the mirror may have a continuous reflecting surface. For example, the mirror 42 may be fabricated as a MEMS (microelectromechanical system) device.

The deformable, dispersive mirror 42 acts as a residual compensator and compensates spatial variations of the group velocity dispersion introduced in the rest of the scanning optical system 10. The multilayer structure of the deformable, dispersive mirror 42 is designed to add a spatially non-uniform group velocity dispersion for pulses impinging on the mirror 42. The spatially non-uniform group velocity dispersion of the mirror 42 has different values for at least the GDD and, in certain embodiments, also for the TOD for different positions on the reflecting surface 48 of the mirror 42. Ray tracing can be used as a method to determine the spatial pattern of the group velocity dispersion of the scanning optical system 10 (exclusive of the dispersion compensating device 25). Based on the GVD pattern of the scanning optical system 10, the multilayer structure of the deformable, dispersive mirror 42 can be suitably designed to eliminate at least partially spatial variations in the GVD pattern.

In certain embodiments, the multilayer structure of the deformable, dispersive mirror 42 is also designed to add a spatially non-uniform group delay for pulses impinging on the mirror 42. The spatial distribution of the group delay added by the multilayer structure can be adjusted by changing the shape of the deformable mirror 42. In other embodiments, the multilayer structure of the deformable, dispersive mirror 42 adds no group delay. In such embodiments, the relative phase of wave packets incident at different positions on the reflecting surface 48 can nevertheless be adjusted by changing the shape of the mirror 42, to thereby introduce a spatially non-uniform group delay pattern for pulses reflected from the mirror 42.

The bulk compensator 46 is, for example, composed of a pair of oppositely disposed dispersive mirrors (not shown in detail). The laser beam 38 enters the space between the mirrors from one side, bounces back and forth between the mirrors for a predetermined number of times, and then leaves the pair of mirrors on the other side. Every reflection of a laser light pulse from one of the mirrors of the pair adds dispersion to the pulse, so that the overall dispersion added to the pulse by the mirror pair depends on the number of bounces experienced by the pulse in the mirror pair. It is to be understood that other configurations of the bulk compensator are likewise conceivable, for example, a single dispersive mirror, a pair of prisms, or a pair of gratings. In certain embodiments, such as where the overall dispersion introduced by the optical system is sufficiently small, the bulk compensator 46 may be omitted and the deformable, dispersive mirror 42 may be the only compensator for compensating the dispersion of the optical system.

As the scanner 26 deflects the laser beam 38, the path length traversed by a ray of the laser beam 38 in the focusing objective 30 and any intermediate air spaces may vary. FIG. 1 shows by way of a dashed line a deflected laser beam 38'. With varying amounts of deflection of the deflected laser beam 38', i.e. with varying values of the scan angle, the spatial pattern of the group delay introduced for a pulse of the deflected beam 38' before it is output from the focusing objective 30 may change. To accommodate for such changes, the control program 36 has instructions to control the actuator device 44 to change the shape of the deformable mirror 42 in accordance with the scan angle. Changing the shape of the deformable mirror 42 has the effect of modifying the relative phase relationship between wave packets incident at different positions on the reflecting surface 48 of the mirror 42. By adjusting the shape of the mirror 42 in an suitable fashion, variations with scan angle of the spatial distribution of the group delay exhibited by a pulse of the deflected beam 38' at an output side of the focusing objective 30 can be reduced to a minimum.

Figure 3:
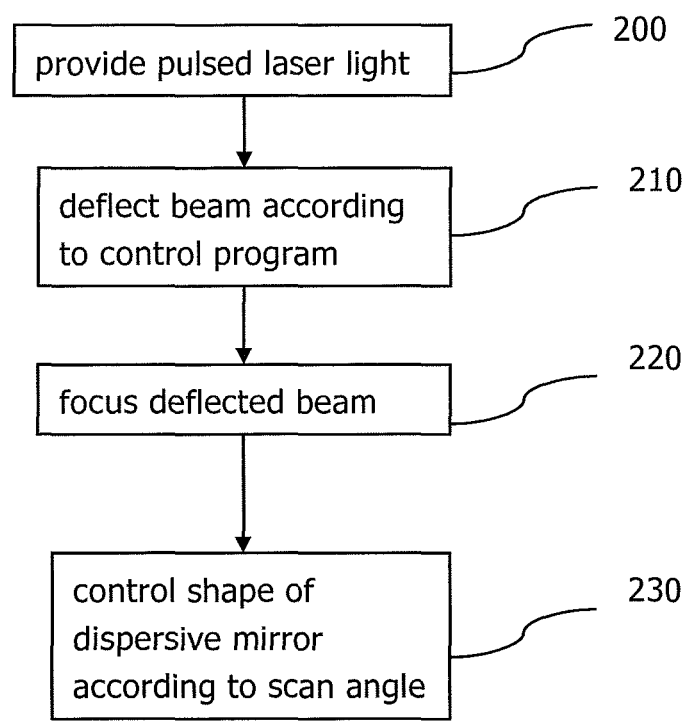
FIG. 3 illustrates steps of a scanning method according to an embodiment.

FIG. 3 is an example of a scanning method which may be performed using the scanning optical system 10. The method can be used for creating an incision in the eye 12. At step 200, a beam 38 of pulsed laser light is provided. At step 210, the beam 38 is deflected transversely, i.e. parallel to an x-y plane, through a scan angle according to a control program 36, resulting in a deflected beam 38'. At step 220, the deflected beam 38' is focused at a target area of the eye 12 to generate LIOB-based photodisruptions in the eye tissue. Based on the scan angle of the deflected beam 38', the shape of a deformable, dispersive mirror 42 is controlled at step 230 to account for variations of the spatial pattern of the group delay introduced by a focusing objective 30 for the pulses of the deflected beam 38', which variations come with different values of the scan angle.

The invention claimed is:
1. A scanning optical system comprising:
an optical source configured to provide a beam of pulsed light of ultra-short pulse duration;

a deflector configured to deflect the beam through a scan angle;

a lens system including a focusing objective configured to focus the deflected beam;

a dispersion compensating device configured to reduce dispersion-related distortion of a pulse of the beam by the lens system, the dispersion compensating device including a deformable, dispersive mirror and an actuator device for the mirror; and a controller configured to control the actuator device to change a shape of the mirror in accordance with the scan angle.

2. The optical system of claim 1, wherein the deformable, dispersive mirror has a multilayer structure providing a dispersion characteristic that varies with position on a reflecting surface of the mirror.

3. The optical system of claim 2, wherein the multilayer structure is configured to introduce at least one of a non-uniform group delay, a non-uniform group delay dispersion, and a non-uniform third-order dispersion across the reflecting surface.

4. The optical system of claim 2, wherein the dispersion compensating device further includes a bulk compensator having a spatially uniform dispersion characteristic for compensating a bulk of at least one of a group delay and a group delay dispersion introduced by the lens system.

5. The optical system of claim 1, wherein the optical source is a laser source and the light has a center wavelength suitable for creating incisions in human eye tissue.

6. A scanning optical system comprising:

an optical source configured to provide a beam of pulsed light of ultra-short pulse duration;

a deflector configured to deflect the beam through a scan angle;

a lens system including a focusing objective configured to focus the deflected beam;

a deformable mirror;

an actuator device for the mirror; and a controller for controlling configured to control the actuator device to change a shape of the mirror in accordance with the scan angle.

7. The scanning optical system of claim 6, wherein the deformable mirror is non-dispersive.

8. The scanning optical system of claim 7, including a dispersion compensating device for reducing dispersion-related distortion of a pulse of the beam by the lens system.

9. The scanning optical system of claim 1, wherein changes of the shape of the mirror as instructed by the controller are designed to accommodate variations of the spatial distribution of a group delay of the optical system, which variations come with different scan angles.

10. A scanning method comprising:

providing a beam of pulsed light of ultra-short pulse duration;

deflecting the beam through a scan angle;

focusing the deflected beam with a focusing objective;

providing a deformable mirror; and controlling a shape of the deformable mirror in accordance with the scan angle to compensate at least partially variations of the spatial distribution of a group delay of the focusing objective versus different scan angles.

* * * * *